United States Patent
Centola et al.

(10) Patent No.: US 10,092,401 B2
(45) Date of Patent: Oct. 9, 2018

(54) CARDIAC VALVE PROSTHESIS DEPLOYMENT SYSTEM

(71) Applicant: NVT AG, Muri, AG (CH)

(72) Inventors: Marcos Centola, Sao Paulo (BR); Emilia Kawa, Hechingen (DE)

(73) Assignee: NVT AG, Muri AG (CH)

( * ) Notice: Subject to any disclaimer, the term of this patent is extended or adjusted under 35 U.S.C. 154(b) by 667 days.

(21) Appl. No.: 14/090,886

(22) Filed: Nov. 26, 2013

(65) Prior Publication Data
US 2014/0088686 A1    Mar. 27, 2014

Related U.S. Application Data

(63) Continuation of application No. PCT/EP2012/059819, filed on May 25, 2012.

(30) Foreign Application Priority Data

Jun. 1, 2011    (EP) .................................... 11168372

(51) Int. Cl.
*A61F 2/06*    (2013.01)
*A61F 2/24*    (2006.01)
*A61F 2/95*    (2013.01)

(52) U.S. Cl.
CPC .......... *A61F 2/2436* (2013.01); *A61F 2/2412* (2013.01); *A61F 2/2418* (2013.01);
(Continued)

(58) Field of Classification Search
CPC ........ A61F 2/95; A61F 2/2418; A61F 2/2436; A61F 2002/9517; A61F 2002/9534;
(Continued)

(56) References Cited

U.S. PATENT DOCUMENTS 5,833,694 A * 11/1998 Poncet ...................... A61F 2/95
                                                                  623/1.11
8,100,958 B2    1/2012 Fischer et al.
(Continued)

FOREIGN PATENT DOCUMENTS

EP     1 964 532 A2    2/2008
WO    2007/098232    8/2007
(Continued)

*Primary Examiner* — Jonathan Miles
*Assistant Examiner* — Mohamed Gabr
(74) *Attorney, Agent, or Firm* — Casimir Jones, S.C.

(57) ABSTRACT

The present invention relates to a deployment system (10) for deploying an expandable cardiac valve prosthesis. The deployment system comprises a first tube (11) being designed to carry an expandable cardiac valve prosthesis; further, a tip (13), being firmly connected to the first tube at a distal end of the first tube, wherein the tip is designed such, that it detachably accommodates and holds a proximal end (21) of a cardiac valve prosthesis (20); a sheath (15) designed to be disposed over and holding the prosthesis (20) in a compressed state, and a first actuating mechanism (16) being linked to the sheath (15) and being slidable in a proximal direction for stepwise retracting the sheath (15). The deployment system (10) further comprises a biasing element being linked to the tip (13), and a blocking mechanism (24), wherein the blocking mechanism is being designed such, that a movement of the first actuating mechanism (16) in the proximal direction relative to the tip (13) is limitable to a maximum path of travel by the blocking mechanism (24).

10 Claims, 7 Drawing Sheets

(52) U.S. Cl.
CPC .............. *A61F 2002/9517* (2013.01); *A61F 2002/9534* (2013.01); *A61F 2230/0054* (2013.01); *A61F 2250/0048* (2013.01); *A61F 2250/0097* (2013.01)

(58) Field of Classification Search
CPC ...... A61F 2002/9522; A61F 2230/0054; A61F 2250/0048; A61F 2250/0097
USPC ............................................... 623/1.11, 2.11
See application file for complete search history.

(56) References Cited

U.S. PATENT DOCUMENTS

| | | | | |
|---|---|---|---|---|
| 2003/0114910 | A1* | 6/2003 | Juhani Laakso | ......... A61F 2/95 623/1.11 |
| 2008/0208209 | A1* | 8/2008 | Fischer | .................. A61F 2/966 606/108 |
| 2009/0024137 | A1* | 1/2009 | Chuter | ..................... A61F 2/95 606/108 |
| 2010/0049313 | A1* | 2/2010 | Alon | .................... A61F 2/2418 623/2.11 |
| 2010/0217382 | A1 | 8/2010 | Chau et al. | |
| 2011/0218619 | A1* | 9/2011 | Benichou | ............. A61F 2/2412 623/2.11 |

FOREIGN PATENT DOCUMENTS

| | | |
|---|---|---|
| WO | 2008/070797 | 6/2008 |
| WO | 2008/138584 | 11/2008 |
| WO | 2009/091509 | 7/2009 |
| WO | 2011/025945 A1 | 3/2011 |
| WO | 2011/139747 A1 | 11/2011 |

\* cited by examiner

CARDIAC VALVE PROSTHESIS DEPLOYMENT SYSTEM

CROSS REFERENCES TO RELATED APPLICATIONS

This application is a continuation of international patent application PCT/EP2012/059819, filed on May 25, 2012 designating the U.S., which international patent application has been published in English language and claims priority from European patent application EP11168372, filed on Jun. 1, 2011. The entire contents of these priority applications are incorporated herein by reference.

BACKGROUND OF THE INVENTION

The present invention relates to a deployment system for deploying an self expandable cardiac valve prosthesis, the deployment system comprising a first tube and being designed to carry an expandable cardiac valve prosthesis to be disposed over a distal portion of the first tube. The deployment system also comprises a tip, being fixedly connected to the first tube at a distal end of the first tube, wherein the tip is designed, such that it removably accommodates and holds a proximal end of a cardiac valve prosthesis, wherein the tip is slidable distally relative to the prosthesis to release the proximal end of the prosthesis. Furthermore, the deployment system comprises a sheath designed to be disposed over and holding the prosthesis in a compressed state, wherein the sheath is slidable proximally relative to the prosthesis to stepwise release and expand the prosthesis, and a first actuating mechanism being slidable in a proximal direction and being linked to the sheath for stepwise retracting the sheath.

Heart valve replacement is necessary where the native heart valve is damaged, mal- or nonfunctioning. In the heart, cardiac—or "aortic"—valves maintain the unidirectional flow of blood by opening and closing depending on the difference in pressure on each side.

The aortic valve can be affected by a range of diseases and can, therefore, require cardiac valve replacement, which means that a patient's aortic valve is replaced by a different valve. The valve can either become leaky, i.e. regurgitant or insufficient, in which case the aortic valve is incompetent and blood flows passively back to the heart in the wrong direction. Further, the valve can become partially shut, i.e. stenotic, in which case the valve fails to open fully, thereby obstructing blood flow out from the heart. The two conditions frequently co-exist.

There are two basic types of artificial heart valve, mechanical valves and tissue valves. Tissue heart valves are usually made from animal tissues, either animal heart valve tissue or animal pericardial tissue, which are treated to prevent rejection and to prevent calcification. Whereas mechanical valves generally are designed to outlast the patient, they have the drawback that due to their material there is an increased risk of blood clots forming, which may only be prevented by a constant anti-coagulant therapy, which makes the patient more prone to bleeding. Mechanical heart valves are generally composed entirely of synthetic or nonbiological materials, whereas tissue (or bioprosthetic) heart valves are composed of synthetic and biological materials. Bioprosthetic cardiac valves can either represent xenografts, which are taken from different species than the recipient, or homografts, which are donor valves taken from the same species as the recipient. Generally, the artificial valves comprise expandable stent systems which are introduced into the vessel in a compressed state and which are allowed to expand by removal of compressive structures.

Aortic valve replacement traditionally requires median sternotomy and thus open heart surgery, which is a major impact on the patient to be treated: The chestbone is sawed in half and after opening of the percardium, the patient is placed on a cardiopulmonary bypass machine. Once the patient is on bypass, the patient's diseased aortic valve is removed and a mechanical or tissue valve is put in its place. Besides the physical stress associated with this operation, there is a risk of death or serious complications from open heart surgery, in particular depending on the health and age of the patient.

However, recently, valves are developed that can be implanted using a catheter or deployment systems without open heart surgery, and the deployment of the prosthesis can either be achieved retrograde, i.e. against normal blood flow, or antegrade, with blood flow.

International patent application WO 2008/070797 discloses a system and a method for transapical delivery of an annulus anchored self-expanding valve. The system disclosed therein comprises a catheter assembly having an outer sheath, an elongate pusher tube and a central tube. At the distal end of the central tube an atraumatic tip is provided; in the loaded state, the prosthesis is carried adjacent to the tip on the central tube and compressed by the sheath. Upon retraction of the sheath, the distal end of the prosthesis, i.e. the one that is located nearest to the tip is released and the prosthesis is allowed to expand. Subsequently, the sheath gets completely pulled back to fully release the prosthesis, which subsequently, in case of as self-expanding prosthesis, can fully expand, or which can be expanded by using a balloon.

Similarly, WO 2007/098232 discloses a deployment device for self-expanding prostheses, wherein the device comprises a split sheath by means of which the prosthesis can be deployed in several steps.

Despite the many different deployment systems and techniques known in the art, the precise deployment with the possibility to move the prosthesis once partially deployed still remains a crucial step and is difficult to achieve with the systems, devices and methods presently available. In addition, a major disadvantage of the presently used systems for deploying self-expandable valves is, that upon deployment the proximal end of the prosthesis, which has to be deployed first, flares and, thus, forms a "parachute" thus obstructing the blood flow. Due to this fact, the operator, e.g. a surgeon, is necessitated to work and deploy the prosthesis under time pressure and fast to avoid disruption of normal blood flow.

SUMMARY OF THE INVENTION

Against this background it is an object of the invention to provide for an improved deployment system by means of which an obstruction of the blood flow, and, thus, an impairment of the heart's natural function, can be prohibited, whilst simultaneously, the deployment system as such should be easy to handle, and allow for precise placement and eventually of correction of a misplaced prosthesis.

According to the invention, this and other objects are achieved by a deployment system as described in detail in the claims.

In particular, with the present invention a deployment system is provided, comprising a first tube comprising a lumen and being designed to carry an expandable cardiac valve prosthesis to be disposed over a distal portion of the first tube; a tip, being fixedly connected to the first tube at a distal end of the first tube, wherein the tip is designed such, that it removably accommodates and holds a distal end of a cardiac valve prosthesis, wherein the tip is slidable distally relative to the prosthesis to release the distal end of the prosthesis; a sheath designed to be disposed over and holding the prosthesis in a compressed state, wherein the sheath is slidable proximally relative to the prosthesis to stepwise release and expand the prosthesis; a first actuating mechanism being linked to the sheath and being slidable in a proximal direction for stepwise retracting the sheath in a proximal direction; the deployment system further comprises a biasing element provided in the proximal portion of the first tube and being linked to the tip, and a blocking mechanism, the blocking mechanism being designed such, that a movement of the first actuating mechanism in the proximal direction relative to the tip is limitable to a maximum path of travel by the blocking mechanism's elements.

In the prior art, and in the present application, the end of the cardiac valve prosthesis (or "heart valve") comprising the valve, is usually called the "proximal end", whereas the end of the heart valve further free from valve material is called the "distal end".

In contrast, the designation of the ends or end portions of the deployment system as distal and proximal is such that the end closer to the operator is designated as "proximal" proximal and the other end further from the operator is designated "distal". Presently and throughout this application, if the expression "proximal" is used in connection with designating a direction, i.e. the "proximal direction", the direction towards the operator is meant. On the other hand, if the expression "distal" is used to describe a direction, i.e. the "distal direction", the direction leading or pointing away from the operator/surgeon/practitioner is meant. Also, when designating the ends of the parts of the deployment system, the term "proximal end" refers to the end that is nearest to the operator, e.g. the surgeon, and the term "distal end" refers to the end opposite to the proximal end and is nearer to the patient to be treated.

With the deployment system according to the invention, the blood flow during deployment of the prosthesis is guaranteed, since a flaring of the proximal end prior to the correct placement is prevented. Also, a deployment of the distal end of the prosthesis prior to the deployment of the proximal end of the prosthesis, which would obstruct blood flow, is successfully prevented. This is achieved by the tip accommodating the proximal end of the prosthesis, and by the fact that the distal end of the prosthesis remains attached and in a compressed state after the proximal end has been released.

Also, this is achieved through the deployment of the medial portion of the prosthesis, i.e. through the controlled, balloon-like release of the medial portion, which allows a precise placement, and even a correction, i.e. back- and forth movement, of the prosthesis during deployment. With this balloon-like deployment, flow of the blood past the prosthesis is guaranteed, which, with the deployment system of the state of the art, is, due to the flared end of the prosthesis, prohibited.

With the blocking mechanism as comprised in the deployment system according to the invention, this balloon-like deployment can be achieved, since the blocking mechanism prevents that the proximal end is deployed before the prosthesis is placed on its precise location. A partial release of the prosthesis is, however, needed, since only with the partial, balloon-like expansion of the prosthesis the dimension and placement of it and its intended location can be assessed.

Preferably, the deployment system further comprises a second actuating mechanism for moving the tip in the distal direction, thus releasing the distal end of the prosthesis. The operator may actuate this second actuating mechanism as soon as the intended site of deployment is reached. Upon actuating the second actuating mechanism, the tip can be moved in the distal direction, thus releasing the proximal end of the prosthesis. Preferably, the tip is engaged with the biasing element, and the tip is, due to the biasing element, released in a resilient or spring-loaded manner, i.e. the tip is, by means of the then stress-loaded spring, briefly pushed in the distal direction and subsequently moved back—due to the stress being relieved from the spring—and into the thus expanded prosthesis.

In a refinement of the present invention, the blocking mechanism comprises a punch element, spring-loaded wing elements, and an abutment element, Presently, the term resilient or "spring-loaded wing element" means any oblong element that aligns with a longish basis and has one of its end attached to the basis, wherein its other end is freely moveable, preferably under a force or pressure-load, away from the basis wherein the other end remains attached to the basis.

Further, the expression "punch element" presently means any element that is suited and designed to press or force apart resilient elements, when moved in between the resilient elements.

The expression "abutment element" presently means any element suitable and designed to provide for a mechanical stop via a face or a wall when another moveable element is moved towards that abutment element.

According to an embodiment of the present invention, the wing-elements are designed such, that their ends that are attached to the basis are located proximally, and that their freely moveable ends are positioned distally.

According to another embodiment of the present invention, the biasing element is a spring, compression spring, or tension spring.

Furthermore, the biasing element is, via the punch, designed to engage with the blocking mechanism.

With this embodiment, the biasing element, upon actuating the second actuating mechanism, is moved in distal direction to release the proximal end of the prosthesis, and subsequently moved into the prosthesis, thus releasing the resilient pressure on the blocking mechanism. Upon the release of the blocking mechanism, the first actuating mechanism may be actuated again and moved further in the proximal direction to fully deploy the prosthesis.

In a preferred embodiment, the punch element of the blocking mechanism is forceable in between the spring-loaded wing elements, thus forcing the freely moveable ends of the wing elements apart, and into a stressed position, with the freely moveable ends of the wings abutting against the abutment element positioned distally from the wing elements, thus blocking the actuating mechanism's path of travel in the proximal direction.

With this feature, it is achieved that the first actuating mechanism cannot move unlimited in the proximal direction, thus preventing that the prosthesis gets fully deployed prior to its correct positioning. The maximal path of travel the first actuating mechanism may travel until it gets blocked by the blocking mechanism corresponds to the maximal length of the prosthesis' balloon-like expansion without one of its proximal or distal ends being released.

In other words, in yet another embodiment of the present invention, the first actuating mechanism and the abutment element are, prior to the deployment of the self-expanding cardiac valve prosthesis, spaced apart from one another in a distance corresponding to a first retraction length of the sheath, the first retraction length of the sheath being such that a medial portion of the prosthesis is released and the proximal and the distal ends of the prosthesis are still covered by the tip and the sheath, respectively.

According to another embodiment, the first actuating mechanism comprises an operator engagable handle.

With "operator engagable handle", a handle is meant which can be directly gripped and manipulated/actuated by the operator, and may include, e.g., a resilient or spring-loaded lever. The lever is connected via a hinge at one of its ends to the body of the actuating mechanism, whereby its other end is freely moveable. In its relaxed state, the spring-load is forcing the freely moveable end angularly away from the basis, whilst its other end remains attached to the basis. The lever or handle can be pressed towards the longitudinal axis against the spring-exerted forces, thus actuating the actuating mechanism.

According to another embodiment of the invention, the first tube comprises a guidewire lumen.

With the guidewire lumen provided in the first tube, the deployment system can be guided over a guide wire, which has firstly been introduced into the vessel of a patient's body, thus facilitating the introduction of the deployment system.

According to yet another development of the invention, the deployment system further comprises a shaft disposed about and concentrically aligned with the first tube, wherein the shaft is non-slidably positioned between the sheath and the first tube, and comprises connecting means for engaging with the distal end of the prosthesis.

The shaft according to the invention represents a pusher or a "back-up" shaft that holds the prosthesis in position when the sheath is being pulled back from the prosthesis, i.e. in the proximal direction. The shaft according to the invention comprises, at its distal end, means for connecting and temporarily holding the distal end of the prosthesis to the shaft. Upon complete removal of the sheath compressing the prosthesis, the distal end of the prosthesis is released from the shaft. Preferably, the connecting means of the shaft is a circumferential, ring-like protrusion located in the distal portion of the shaft, preferably in a certain distance from the very distal end of the shaft. The distal end of the prosthesis can be placed over the protrusion and the sheath compressing the prosthesis may be placed over the thus temporarily hooked end of the prosthesis, thus preventing the end of the prosthesis to move with the sheath upon its removal.

According to yet another embodiment, the deployment system further comprises a tubular knurled or toothed rod disposed about and concentrically aligned with the proximal portion of the sheath. The lever of the first actuating mechanism engages with the tubular rod, thus allowing for a stepwise retraction of the sheath upon actuation of the lever/first actuating mechanism.

In a preferred embodiment, the rod comprises at least one fixation element by means of which, preferably with its proximal end, it can be releasably attached within the abutment element. Upon engagement with the abutment element, the tubular rod cannot be moved relative to the abutment element and vice versa.

Preferably, the proximal end of the rod comprises two at least partially resilient fixation elements pointing outward from a longitudinal axis of the rod and engaging with the abutment element. In this connection, the expression "resilient" means, that the fixation elements can be transferred from a pressure-free/unloaded position where it/they is/are engaging the abutment element/the housing of the abutment element and where it/they is/are pointing away from the longitudinal axis of the rod, to a pressure-loaded position, where they are moved towards the axis of the rod, thus detaching from the engagement with the abutment element. Thus, the fixation elements represent protrusions, projecting away and outwardly from a longitudinal axis of the tubular rod. Via this/these fixation element(s), the rod is attached to the abutment element, and, as a consequence, this/these stop element(s) are blocking the abutment element to move in proximal direction. Thus, the attachment of the rod within the abutment element represents an additional safety means, preventing a premature release of the prosthesis.

Preferably, there are provided two fixation elements which are positioned opposite from one another on the circumference of the rod.

With this measure, an outer housing for the sheath is provided accommodating the proximal end of the sheath therein; the actuating mechanism, being connected with the proximal end of the sheath can, upon its actuation, slide over the second tube.

It is particularly preferred if the deployment system comprises a cardiac valve prosthesis to replace a diseased or malfunctioning native heart valve of a patient in need thereof.

The invention further relates to a cardiac valve prosthesis for replacement of the native valve of a human body, which may be deployed with the deployment system according to the invention. The cardiac valve prosthesis according to the invention comprises an expandable generally cylindrical stent support having a plurality of diamond shaped expandable cells, and having a proximal end, a proximal portion, a medial portion, a distal portion, and a distal end, wherein at the distal end of the stent support, at least three of the outermost and free edges of the diamond shaped expandable cells, pointing in the distal direction, have a t-bar-like ending, wherein the medial portion of the stent support carries radiopaque markers, and wherein the size of the cells in the distal portion is greater than the size of the cells in the proximal portion. Further, the prosthesis according to the invention comprises a valve having a plurality of leaflets, and a plurality of commissure points, and wherein the valve is mounted on the stent support, such, that the valve forms the inner surface of the stent support, and that in the proximal portion a sealing zone is formed, wherein the inner surface of the cylindrical stent support is lined with the valve, wherein the valve is, in a region between the distal end and the medial portion, fixed to the stent support via the commissure points, and wherein the stent support has, in a region between the distal end and the medial end, a valve-free portion.

The prosthesis according to the invention is particularly suited for introduction into the heart via the deployment system according to the invention. The particular shape of the prosthesis in connection with the t-bar-like ending of the prosthesis allows for an easy and precise loading of the prosthesis onto/in the deployment system as well as for a precise deployment at the site of interest. Also, with the radiopaque markers, the correct and precise positioning of the prosthesis may be easily observed, e.g. by means of X-ray during its deployment.

The cardiac valve prosthesis according to the invention is particularly suited for employment with the deployment system according to the invention. The cardiac valve prosthesis and the deployment system are interoperating such, that when the deployment system has been actuated to bring the prosthesis loaded thereupon is in a balloon-like release state, the native valve can still be passed which allows for a very precise positioning. Also, the prosthesis is fully reloadable, since in case its removal or replacement should be necessary, it can be retracted back into the sheath.

Further, once the proximal end of the prosthesis, which is, in its loaded state, fixed within the tip, is released, the tip can be moved within the expanded end of the prosthesis. As a consequence, the tip is prevented from interfering with the valve material which might otherwise lead to a damaging of the prosthesis.

Also, with the very specific design of the cardiac valve prosthesis, formation of a "parachute", which might obstruct the blood flow, is avoided, since the prosthesis can be positioned exactly at the desired site and upon deployment of the proximal end the prosthesis is fully functioning.

According to a preferred embodiment of the cardiac valve prosthesis according to the invention, at the distal end, the cylindrical shape of the stent support in the valve-free portion has a diameter that is reduced compared to the remaining cylindrical shape of the stent support.

In a preferred embodiment, the cardiac valve prosthesis comprises bovine pericardium.

Also, in a refinement of the prosthesis according to the invention, at the fixation site of the commissure points of the valve the at the stent support, the cylindrical shape of the stent support has the largest diameter compared to the remaining cylindrical shape.

This feature ensures a tight attachment of the cardiac valve prosthesis at the insertion site, namely where the attachment is crucial, and it is thus prevented that the prosthesis moves out of place.

The invention also concerns a method for releasing a cardiac valve prosthesis loaded on a deployment system, the method comprising the steps of:
  providing a deployment system according to the invention, comprising an expandable cardiac valve prosthesis according to the invention,
  actuating the first actuating mechanism of the deployment system, and, thus, stepwise retracting the sheath and simultaneously moving the actuating means in the proximal direction until the actuating mechanism abuts the blocking mechanism, whereupon the punch element is forced in between the resilient wing elements, thus forcing them apart and blocking further movement of the actuating mechanism and the retraction of the sheath, thus,
  releasing a medial portion of the prosthesis, whereby the proximal end of the prosthesis remains fixed within the tip, and the distal end of the prosthesis remains fixed in the distal end of the shaft, thereby permitting a balloon-like expansion of the prosthesis,
  moving the tip and, thus, releasing the proximal end of the prosthesis, whereby the pressure on the biasing element is relieved, thus withdrawing punch element from in between the resilient wing elements, thus releasing the resilient wing elements into an unstressed position, and
  fully retracting the sheath and fully deploying and releasing the expandable prosthesis.

With the method according to the invention, a precise placement of the prosthesis is possible. Also, employing the method of the invention allows the practitioner or surgeon to carefully place and even re-place the prosthesis, without being under time pressure for timely positioning the prosthesis in order not to obstruct blood flow. Since with the method according to the invention, a balloon-like intermediate step of deploying the prosthesis is generated, flow of blood past the prosthesis is guaranteed, thus providing time for a deliberate deployment of the prosthesis. Further, with the method according to the invention, flaring of the released end of the prosthesis is prohibited.

According to a refinement of the invention, the method further comprises, after the providing-step, the step of:
  positioning the deployment system such, that the prosthesis is in the area of the cardiac valve to be replaced by the prosthesis.

Preferably, in the method according to the invention, the distally moving of the tip is achieved by actuating a second actuating mechanism.

It is understood that the features described hereinabove and those still to be described below fall within the scope of the present invention not only in the respectively specified combinations, but also in different combinations or on their own.

Further features follow from the description and the preferred embodiments.

BRIEF DESCRIPTION OF THE DRAWINGS

Preferred embodiments are shown in the Figures and are described in further detail hereinbelow.

In the figures:

FIG. 2 shows the deployment system of FIG. 1, with the prosthesis partially deployed, in an intermediate step of the deployment, not drawn to scale (A); an enlarged detail of an proximal portion of the deployment system shown in the position as depicted in FIG. 2A (B), FIG. 3 shows the deployment system of FIG. 1/2, with the prosthesis deployed at its proximal end (A); an enlarged detail of an proximal portion of the deployment system shown in the position as depicted in FIG. 3A (B);

DESCRIPTION OF PREFERRED EMBODIMENTS

Figure 1:
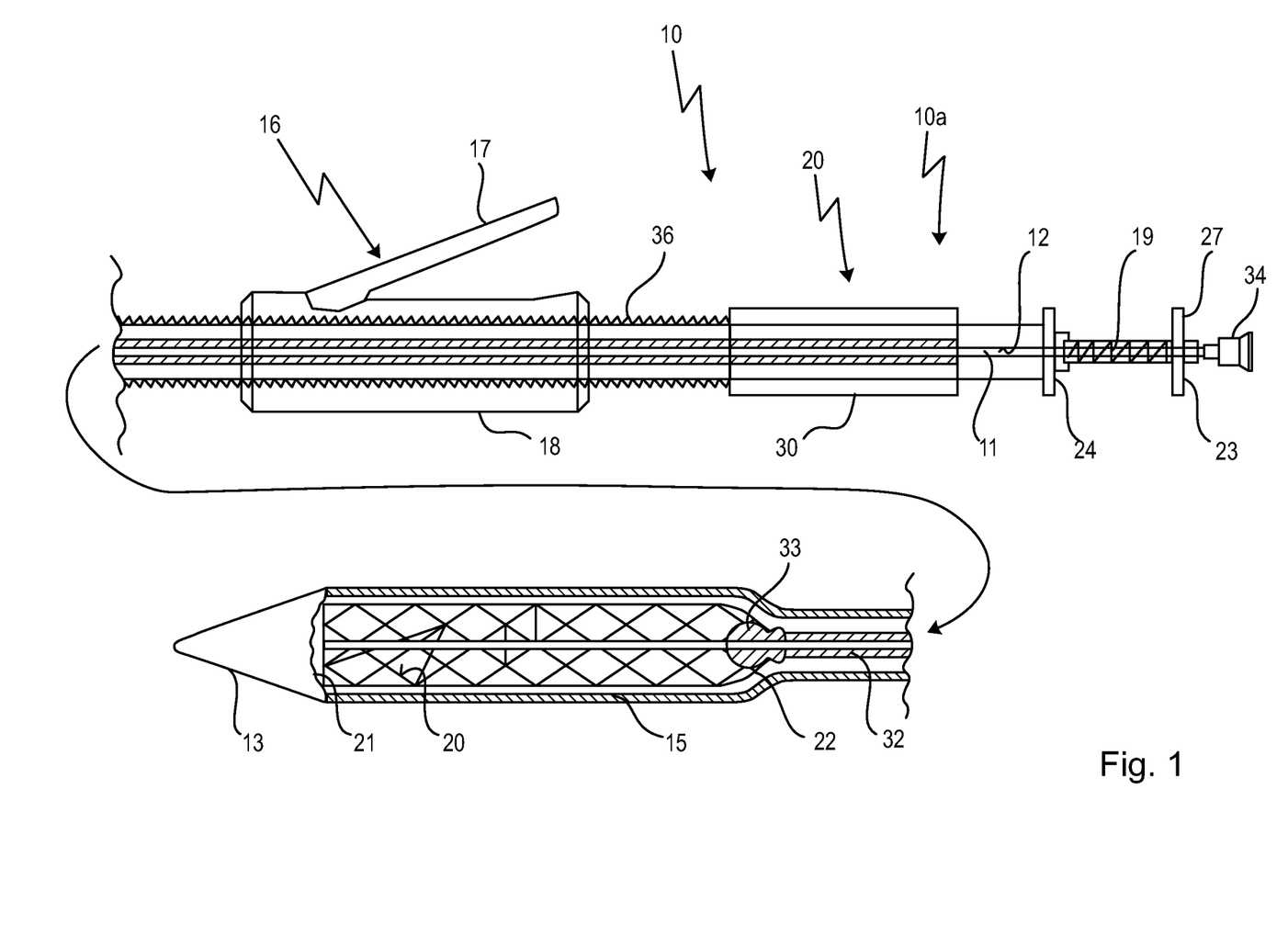
FIG. 1 shows, in longitudinal section, an embodiment of a deployment system according to the invention, not drawn to scale, with the prosthesis loaded on the deployment system.

In FIG. 1, an embodiment of the deployment system according to the invention is generally designated with 10. The deployment system 10, not drawn to scale and showing a proximal portion 10a and a distal portion 10b of the deployment system, comprises a first tube 11, having a lumen 12 designed for accommodating a guidewire (not shown). In FIG. 1, the deployment system 10 has loaded thereupon a prosthesis 20, which is carried by and loaded onto a distal portion 11a of the tube 11. The tube 11 has, on its very distal end, a tip 13 representing an atraumatic tip, having, on its side facing towards the proximal direction, means for accommodating and detachably holding a proximal end 21 of the prosthesis 20.

The deployment system 10 further comprises an outer sheath 15, holding and compressing the prosthesis 20 in its compressed state when loaded on the first tube 11. The outer sheath 15 is slidable/retractable in proximal direction, i.e. towards the operator, in order release the prosthesis and to allow its expansion. The outer sheath 15 is linked to a first actuating mechanism 16, the actuating mechanism 16 being slidable in a proximal direction for stepwise retracting the sheath 15.

The actuating mechanism 16 comprises a lever 17, linked to a tube-like grip 18, which is disposed about the outer sheath 15. Internally of the grip 18, the outer sheath 15 is attached within the grip 18. The lever 17 is, by means of a spring-loaded mechanism (not shown) attached, via one of its ends 17a and via a hinge (not shown) to the grip 18. Its other end 17b is freely moveable from a closed, stress-loaded position, where the lever 17 is approached to the grip 18, to an open, stress-relieved position, where the spring/hinge keeps and forces the lever 17 angularly away from the grip 18. By stepwise actuating the actuating mechanism 16, i.e. by repeatedly pressing down the lever 17, the sheath 15, connected with the grip 18, is stepwise retracted.

As can be seen in FIG. 1, the deployment system 10 further comprises a biasing element 19 provided in the proximal portion 10A of deployment system 10 and being linked to the tip 13. The biasing element 19 is securely placed and provided between two holding elements, a proximal holding element 23 and a distal holding element 24, which are, in a defined distance from one another, placed over the first tube 11. Holding element 23 represents a second actuating mechanism 27, which will be explained further below.

The deployment system 10, in addition, comprises a blocking mechanism 25, having a punch element 26, resilient or spring-loaded wing elements 28, and an abutment element 30. The distal holding element 24 is engaged with the punch element 26 and the resilient wing elements 28.

Further, a shaft 32 is provided, disposed about and concentrically aligned with the first tube 11, wherein the shaft 32 is non-slidably positioned between the sheath 15 and the first tube 11, and comprises connecting means 33 for engaging with the distal end 22 of the prosthesis 20. The connecting means 33 is, in the exemplary embodiment depicted in the figures, a circumferential ring-like protrusion placed about the distal portion of the shaft 32 in a certain distance from the very distal end of the shaft 32. The distal end 22 of the prosthesis 20 can be detachably hooked onto this protrusion/connecting means 33.

Also provided in the deployment system 10 according to the invention is a second actuating means 27, representing, in the exemplary embodiment shown in the figures, a knob, directly linked with the tip and being located at the proximal end of the first tube. The knob may be pushed in the proximal direction to actuate the tip 13, whereby the tip 13 gets pushed first in the distal direction to release the proximal end 21 of the prosthesis 20, and subsequently gets drawn back, i.e. in the proximal direction and into the then open and expanded proximal end 21 of the prosthesis 20, which movement of the tip 13 is effected by the biasing element 19.

In the FIGS. 1 to 4, reference number 34 designates the adaptor for the guide wire lumen.

References sign 36 designates a knurled or toothed tubular rod, which is positioned concentrically about the sheath and which interoperates with the actuating mechanism 16, in particular with the lever 17, such that a stepwise retraction of the sheath is allowed upon actuating the actuating mechanism 16. The lever 17 is, via its end 17a engaging with the knurled rod. The rod 36 is, with its proximal end (see FIG. 5) attached within the abutment element 30. For clarity reasons, the rod 36 is only shown in FIG. 1A, and not in the FIGS. 2 and 3.

Figure 2A:
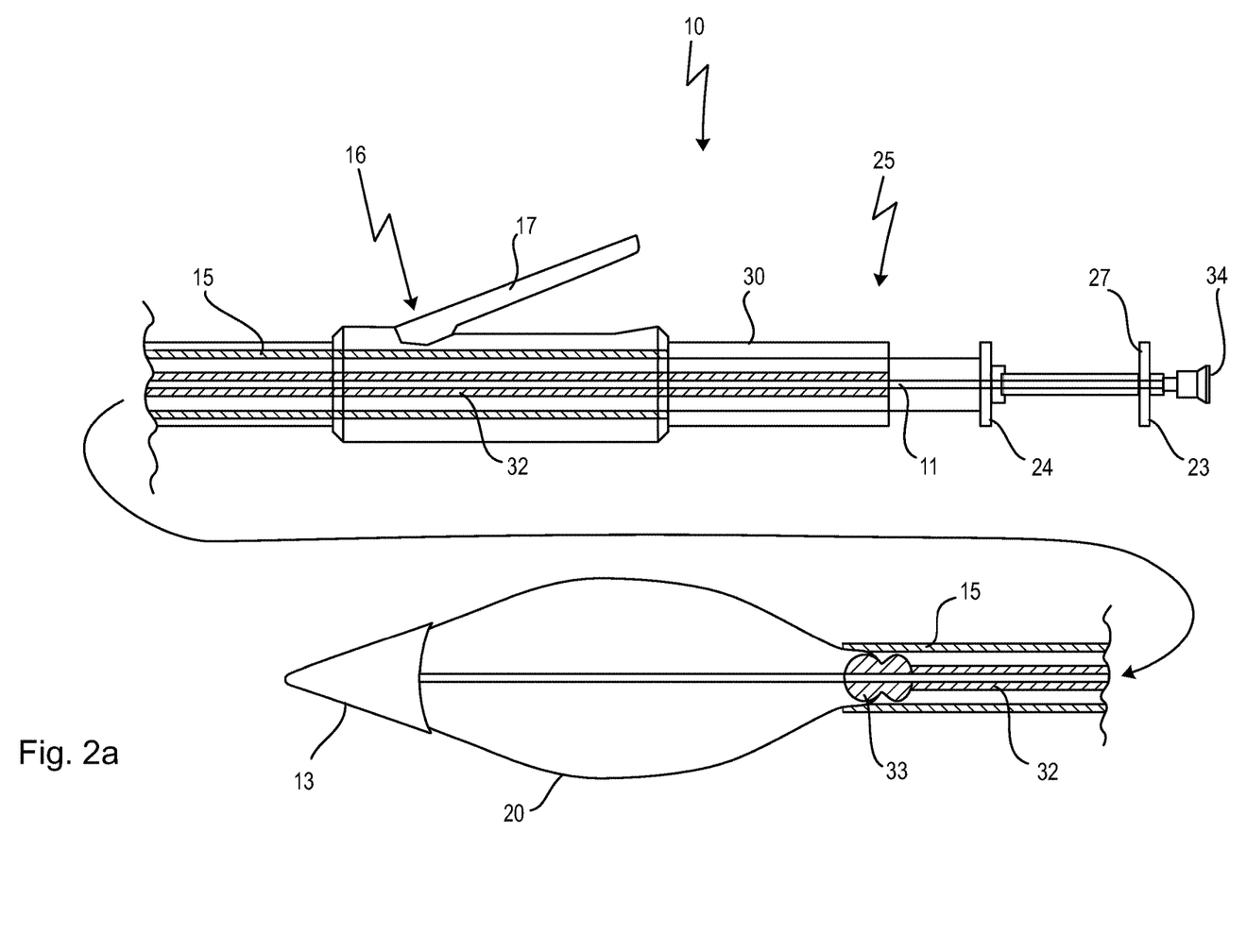
Figure 2B:
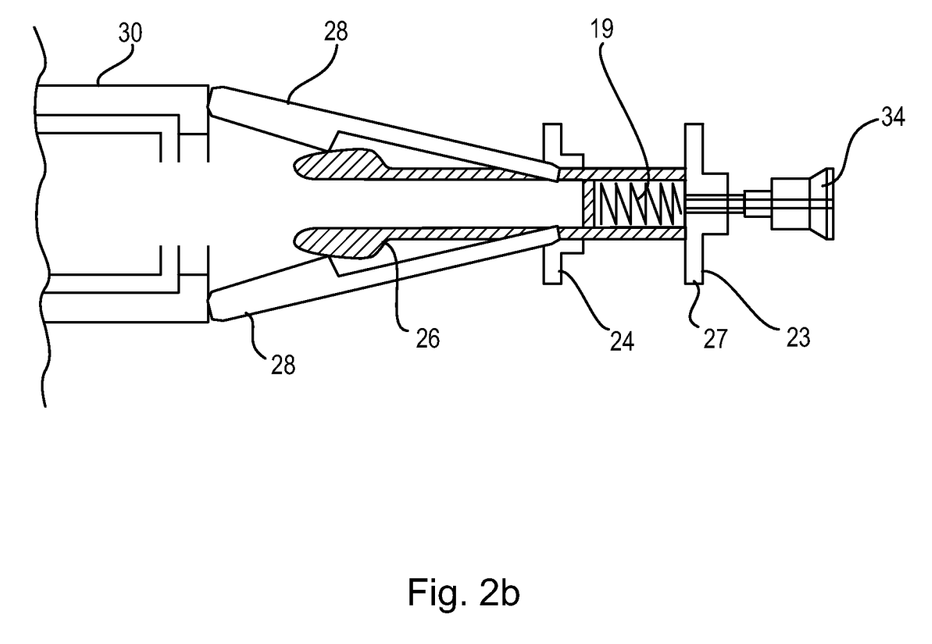
Figure 3A:
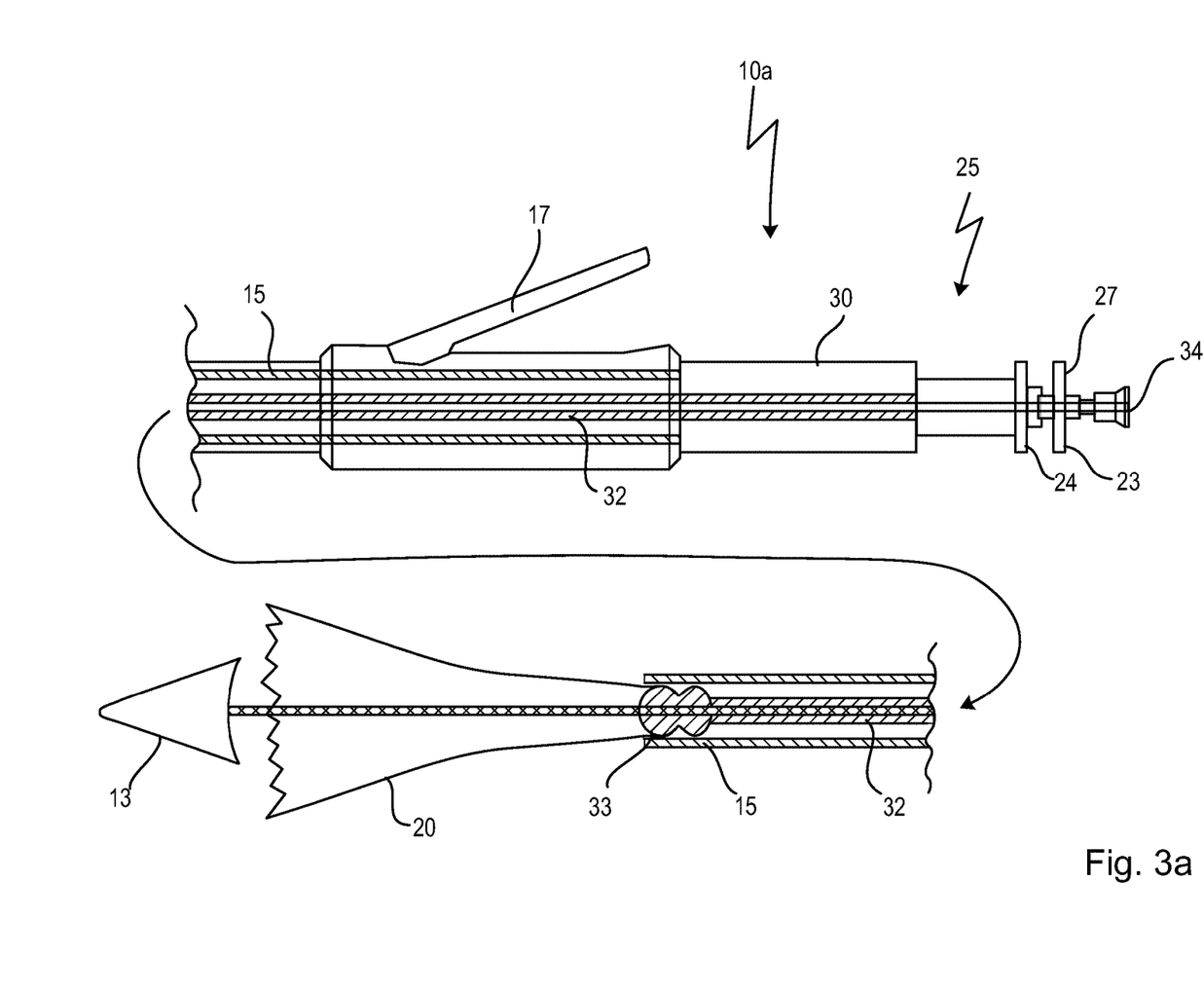
Figure 3B:
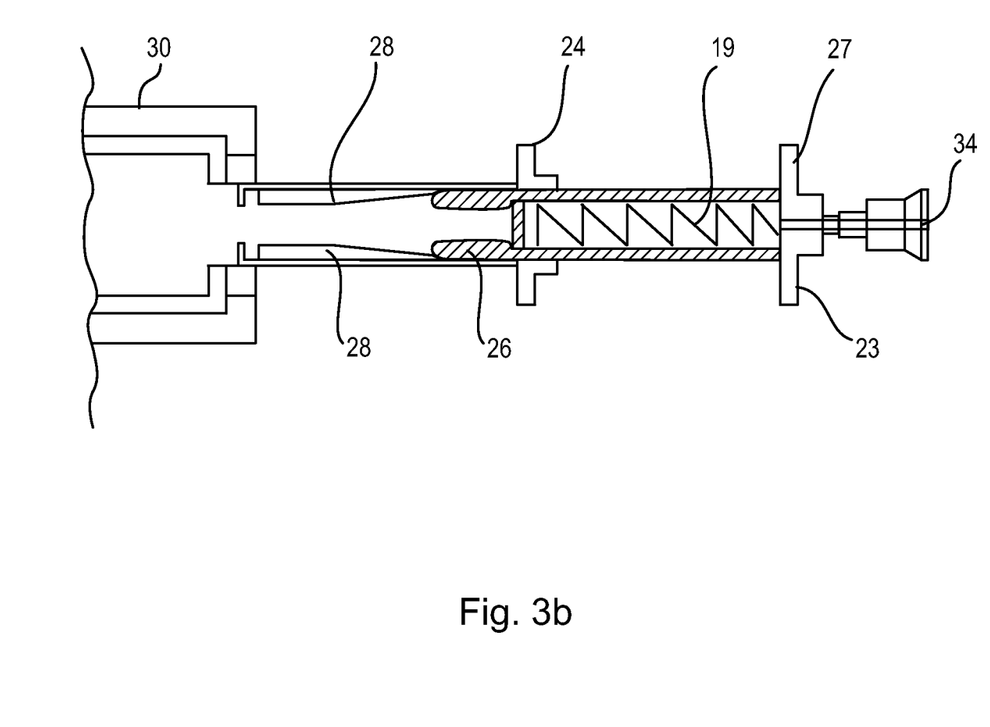

In FIGS. 2 and 3, deployment steps for deploying—at least partially—the prosthesis are shown:

The blocking mechanism 25 is designed such, that a movement of the first actuating mechanism 16 in the proximal direction relative to the tip 13 is limitable to a maximum path of travel by the blocking mechanism 25. This is achieved by the interaction of the first actuating mechanism 16 with the blocking mechanism 25 and is shown in FIG. 2A: Upon actuation of the first actuating mechanism 16, i.e. by pressing down the lever 17 towards the grip 18, the first actuating mechanism 16 is stepwise moved in proximal direction; the movement of the actuating mechanism 16 in proximal direction is then stopped when it abuts the abutment element 30, which serves as a safety locker.

This is also due to the fact that the biasing element 19 interacts with the punch element 26 and exerts pressure on the punch element 26, since the biasing element 19 gets stress-loaded through the abutment of the actuating mechanism 16 on the abutment element 30, which can be seen in FIG. 2B.

As can also be taken from FIG. 2A, the prosthesis 20 gets, upon stepwise movement of the actuating mechanism in the proximal direction, stepwise released in a medial portion, whilst its proximal end 21 and its distal end 22 remain affixed to the tip 13 and the distal end of the shaft 32, respectively. In this way, the prosthesis 20 expands in a balloon-like manner, facilitating flow of the blood past the prosthesis 20, thus not obstructing the normal blood flow through the heart.

Further, with the prosthesis 20 not completely expanded and still fixed with its proximal 21 and its distal 22 end, a precise positioning of the prosthesis 20 is still possible, i.e. movement and shifting of the balloon-like expanded prosthesis 20 can be performed to correctly place the prosthesis 20. Also, if a reloading of the prosthesis 20 into the deployment system 10 should be necessary or wanted, the sheath 15 may be simply repositioned over the medial portion of the prosthesis 20, by moving the first actuating mechanism 16 in the distal direction.

In a next deployment stage, which is depicted in FIG. 3, the knob, i.e. the second actuating mechanism 27 is actuated, thereby moving the tip 13, in a spring-loaded manner, in the distal direction to release the proximal end 21 of the prosthesis 20. Due to the biasing element 19 and the spring-loaded force, the tip 13 gets subsequently moved back into the then open and expanded proximal end 21 of prosthesis 20. The prosthesis 20 is, upon release of its proximal end 21, which comprises the valve, fully functional and starts to work. In that way, blood flow gets, at no point of the deployment, obstructed by the deployment or introduction of the prosthesis 20.

With the tip 13 moving inside the prosthesis 20, the punch element 26 is shifted into its most proximal position, thereby moving out from in between the spring-loaded wing elements 28. As a consequence, the spring-loaded wing elements 28 are centred back towards their basis, thus no longer blocking the abutment element 30. This can be taken in detail from FIG. 3B.

In case the tip 13 should jam with or in the prosthesis 20 and should, therefore, not be moved into/inside the prosthesis 20, the punch element 26 is not shifted into its most proximal position, thereby still forcing the wing elements 28 apart and against the abutment element 30, thus still blocking the abutment element 30. In that way, the deployment system 10 according to the invention provides for an additional safety mechanism, which guarantees that the distal end 22 of the prosthesis 20 cannot be deployed before the proximal end 21 of the prosthesis 20 has been correctly released. To release the eventually jammed tip 13, the knob or second actuating mechanism 27 has simply to be pushed another time taking care that the tip 13 does not get jammed again.

As a next deployment stage, and in case the tip 13 is in the correct position, the abutment element 30, together with and driven by the first actuating mechanism 16 abutting against the abutment element 30, can be moved in the proximal direction, whereby the sheath 15 gets completely retracted, releasing and freeing the distal end 22 of the prosthesis 20.

The method according to the invention by means of which the prosthesis 20 gets deployed in a heart of a patient in need thereof, which may be a human or any other mammal, comprises the deployment steps described above in connection with the description of the figures.

Generally, as a first step, a guidewire is introduced via blood vessels and advanced into the heart. Subsequently, the deployment system 10 the elements of which are carrying and holding the prosthesis 20 in a compressed state is inserted over the guidewire, whereby its advancement is being controlled by, e.g., X-ray or other radiographic means. The very proximal end 21 of the prosthesis 20 is detachably attached to the tip 13, the very distal end 22 is detachably fixed to connecting means 33 in the distal portion of the shaft 32, and the prosthesis 20 is overall covered by the sheath 15, which compresses and restrains the prosthesis 20.

As soon as the operator/practitioner/surgeon is of the opinion that the prosthesis 20 is correctly placed, he actuates and moves the first actuating mechanism 16 in the proximal direction, thus stepwise retracting the sheath 15, whereby the medial portion of the prosthesis 20 is allowed to expand. In a second deployment stage, the first actuating mechanism 16 abuts the abutment element 30, and the biasing element 19, which is connected with the tip 13, forces the punch element 26 in between the wing elements 28, forcing them apart and blocking any further proximal movement of the first actuating mechanism 16 and abutment element 30. The prosthesis 20 may now be precisely placed (or even reloaded, if necessary) by moving the deployment system 10, and thereby the prosthesis 20, back and forth.

In a third deployment stage, the proximal end 21 of the prosthesis 20 is released by actuating the second actuating mechanism 27/knob, which is directly connected with the tip 13. In doing so, the tip 13 springs in distal direction and thus releases the proximal end 21 of the prosthesis 20, and moves, subsequently back in proximal direction and into the opened and expanded prosthesis 20.

With the tip 13 now being located inside the prosthesis 20, the punch element 26 gets moved in its most proximal position, thus moving out from between the forced-apart wing elements 28, whereby the wing elements 28 get—due to their spring load—forced back and aligned towards their base. As a consequence, the abutment element 30 as well as the first actuating mechanism 16 are not blocked anymore and may be moved in proximal direction to retract the sheath 15 and to fully release the prosthesis 20.

The safety measures that are provided with the deployment system 10 according to the invention are, thus, a guarantee that the proximal end 21 of the prosthesis 20 gets deployed before the distal end 22 of the prosthesis 20; that the prosthesis end does not flare upon deployment and, thus, does not obstruct blood flow, allowing a more precise and controllable placement of the prosthesis 20; and that back and forth movements of the prosthesis 20 are possible, crossing the native valve, due to the balloon-like shape of the partially deployed prosthesis 20.

Furthermore, the prosthesis 20 may be reloaded when in the balloon-like stage, if necessary. Also, with the movement of the tip 13 inside the prosthesis 20, the tip 13 does not drag or otherwise interfere—and potentially damage the valve—with the prosthesis, but rather allows for a smooth retraction and removal of the deployment system 10, including the tip 13.

In addition, the deployment step of forming a balloon-like expanded prosthesis 20 allows for a better orientation of the prosthesis 20 and for a more precise placement in the heart.

Figure 4:
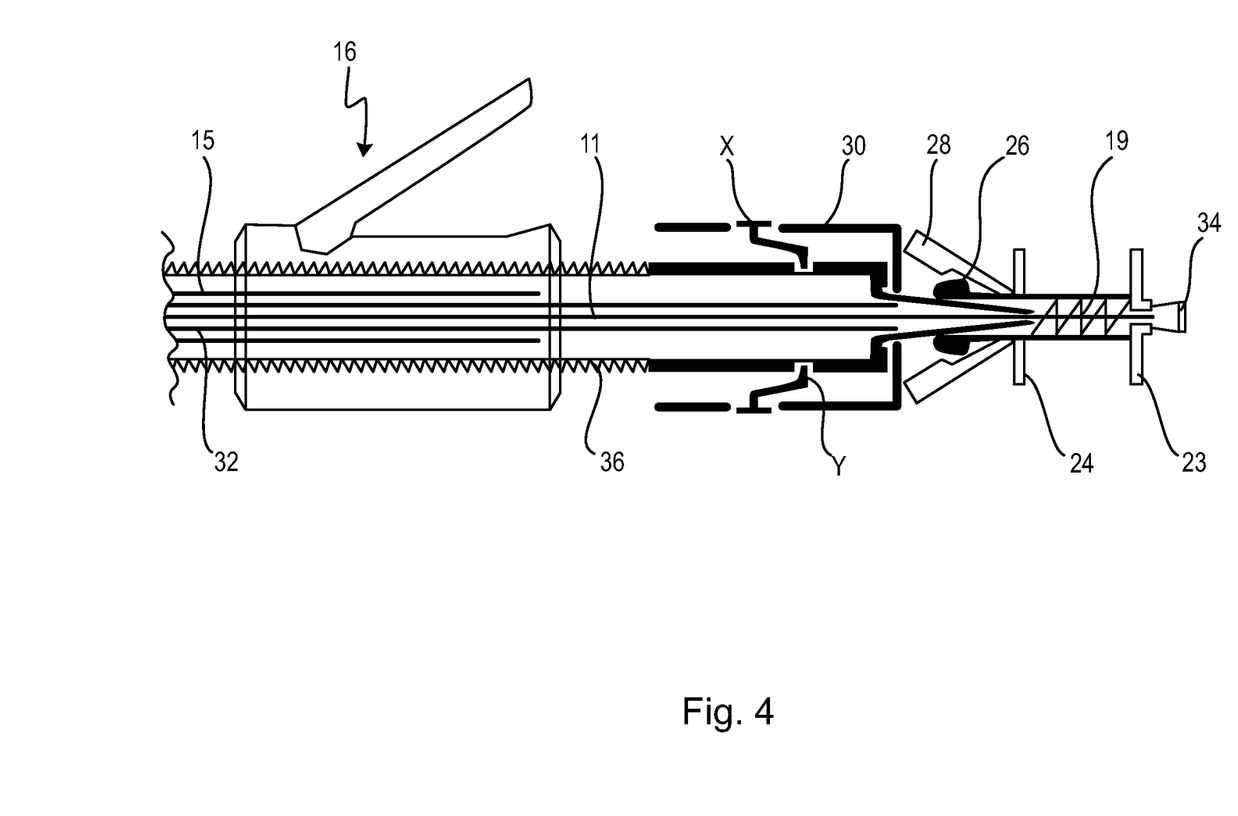
FIG. 4 shows an enlarged detail of the proximal end of another embodiment of the deployment system according to the invention.

In FIG. 4, another embodiment of the present invention is shown, where the same elements as have already been shown in FIGS. 1 to 3 are designated with the same reference signs. FIG. 4 shows, in a more detailed fashion, the proximal end 10a of a deployment system 10. As can be seen in FIG. 4, the tubular rod 36 is attached within a housing of the abutment element 30 by means of two fixation elements 37, 38, which, in the embodiment shown in FIG. 4, are positioned opposite to one another on the circumference of the tubular rod 36. The fixation elements 37, 38 represent protrusions, which project away and outwardly from a longitudinal axis of the rod; they engage with the abutment element 30, thereby preventing a movement of the abutment element 30 in a proximal direction. In that way, an additional safety mechanism is provided, preventing a premature deployment of the prosthesis.

When the operator has deployed the prosthesis 20 such, that it has expanded in a balloon-like shape, i.e. such, that its proximal end 21 is still fixed in the tip 13, and the distal end 22 is covered by the outer sheath 15, the actuating mechanism 16 is abutting the abutment element 30. In order to proceed with the deployment of the prosthesis 20, the operator actuates the second actuating mechanism 27 thus releasing the proximal end 21. In order to be able to move the abutment element 30, the two fixation elements 37, 38 are pressed towards the axis of the rod by the operator and pulled in a proximal direction. As a consequence, the first actuating mechanism 16 comprising the grip 18 is free to move proximally.

Figure 5:
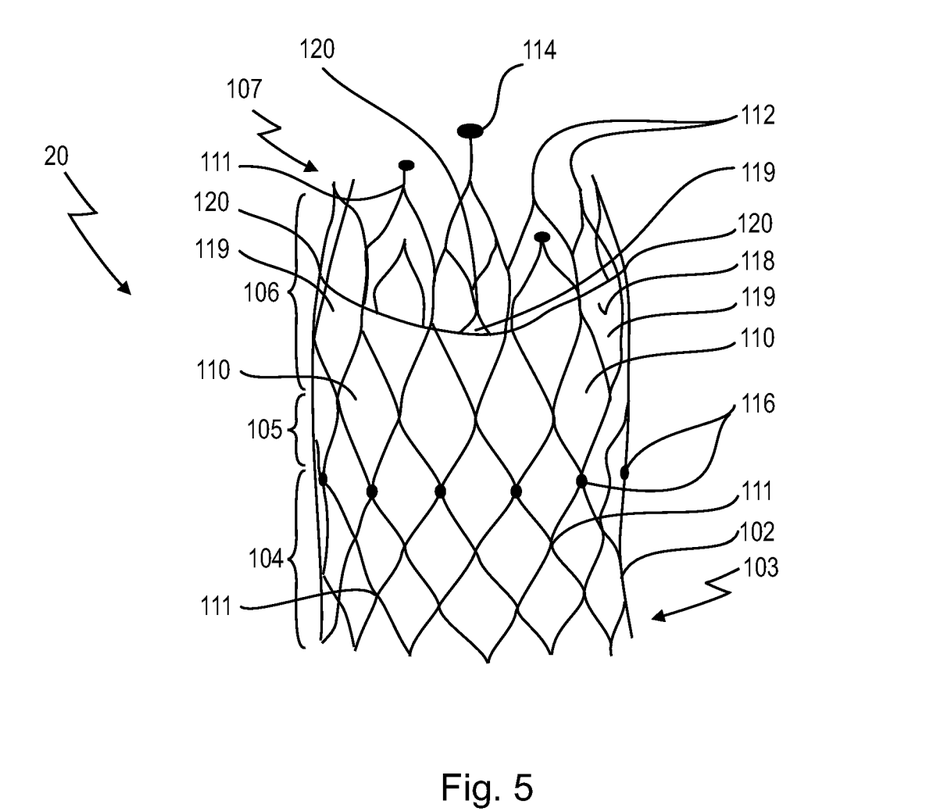
FIG. 5 shows an embodiment of the cardiac valve prosthesis according to the invention in the expanded state.

The cardiac valve prosthesis 20 according to the invention is depicted in more detail in FIG. 5:

The prosthesis 20 has an expandable generally cylindrical stent support 102 comprising a plurality of diamond shaped expandable cells 110 having edges 111, wherein the stent support 102 has a proximal end 103, a proximal portion 104, a medial portion 105, a distal portion 106, and a distal end 107. The diamond shaped expandable cells are either laser-cut or formed by interweaving or braiding metal wires. At the distal end 107 of the stent support 102, the cells 110 have free edges 112, i.e. edges that are not connected or adjacent to or forming edges with another cell. At least three of the free edges 112 of the diamond shaped expandable cells 110 pointing in the distal direction have a T-shaped ending 114.

Presently, with the expression "T-shaped" any form or design of the free edge 112 of a cell 110 is meant, which has the shape of the letter "T", i.e. one straight (orthogonal with respect to the prosthesis body) metal wire section and another metal wire section that is perpendicular placed at the very end of the orthogonal wire section.

Further, as can be seen from FIG. 5, the medial portion 105 of the stent support 102 carries radiopaque markers 116, thus facilitating the orientation and placement of the prosthesis 20. In addition, the size of the cells 110 in the distal portion 106 of the stent support 102 is greater than the size of the cells 110 in the proximal portion 104 of the stent support 102.

The prosthesis 20 also comprises a valve 118 having a plurality of leaflets 119, and a plurality of commissure points 120. The valve 118 is attached to the stent support 102, such, that the valve 118 forms the inner surface of the stent support 102, thus, forming, in the proximal portion 104, a sealing zone, wherein the inner surface of the cylindrical stent support 102 is lined with the valve 118.

The material of the stent support 102 is preferably Nitinol or any other metal with shape-memory characteristics. The valve may be a donor valve, e.g. an valve from a mammal, or an artificial valve, as outlined above.

Further, in the prosthesis 20 according to the invention, the valve 118 is, in a region 108 between the distal end 107 and the medial portion 105 of the stent support 102, fixed to the stent support 102, namely via its commissure points 120. The stent support 102 has further, in a region 108 between the distal end 107 and the medial portion 105, a valve-free portion.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not restricted except in light of the attached claims and their equivalents.

What is claimed is:

1. A deployment system (10) for deploying a cardiac valve prosthesis, the deployment system comprising:
    a first tube (11) having a distal end and a proximal end, wherein the first tube comprises a lumen (12) configured to carry a cardiac valve prosthesis, wherein the cardiac valve prosthesis is capable of disposal over a distal portion (11a) of the first tube (11), wherein the cardiac valve prosthesis is capable of compression or expansion;
    a tip (13) fixedly connected to the distal end of the first tube, wherein the tip is configured to detachably accommodate and hold a proximal end (21) of the cardiac valve prosthesis (20), wherein the tip (13) is configured to slide distally relative to the cardiac valve prosthesis (20) resulting in a release of the proximal end (21) of the cardiac valve prosthesis (20),
    a sheath (15) disposed over and holding a cardiac valve prosthesis (20) in a compressed state, wherein the sheath (15) is configured to slide proximally relative to the cardiac valve prosthesis (20) resulting in a release and expansion of the cardiac valve prosthesis (20),
    a first actuating mechanism (16) comprising a lever (17) and a tubular grip (18), wherein the tubular grip is disposed about the sheath (15) such that the sheath is attached within the tubular grip, wherein actuation of the first actuating mechanism permits the first actuation mechanism to slide over the first tube in a proximal direction thereby resulting in a stepwise retraction of the sheath, wherein such retraction of the sheath permits expansion of the cardiac valve prosthesis,
    a biasing element (19) positioned in the proximal portion (11b) of the first tube (11) and being directly linked to the tip (13), and
    a blocking mechanism (25) comprising a punch element (26), two spring-loaded wing elements (28), and an abutment element (30), wherein the blocking mechanism is positioned over the first tube between the distally positioned first actuating mechanism and the proximally positioned biasing element, wherein the blocking mechanism is capable of preventing movement of the first actuating mechanism (16) in a proximal direction relative to the tip (13) beyond the blocking mechanism (25).

2. The deployment system (10) according to claim 1 further comprising a second actuating mechanism (27) comprising a knob directly linked with the tip (13), wherein actuation of the second mechanism permits movement of the tip (13) in a distal direction thereby resulting in a release of the proximal end (21) of the cardiac valve prosthesis (20).

3. The deployment system (10) according to claim 1, wherein the punch element (26) is capable of movement between the two spring-loaded wing elements (28) resulting in a forcing of the two spring-loaded wing elements apart and into a stressed position abutting against the abutment element (30) thereby blocking the first actuating mechanism's (16) path of travel in the proximal direction.

4. The deployment system (10) according to claim 1, wherein the first actuating mechanism (16) and the abutment element (30) are, prior to the deployment of the cardiac valve prosthesis (20), spaced apart from one another in a distance corresponding to a first retraction length of the sheath (15), the first retraction length of the sheath (15) being such that a medial portion of the prosthesis (20) is released and the proximal (21) end of the prosthesis (20) is covered by the tip and the distal end (22) of the prosthesis (20) is still covered by the sheath (15).

5. The deployment system (10) according to claim 1, wherein the biasing element (19) is designed, via the punch element (26), to engage with the blocking mechanism (25).

6. The deployment system (10) according to claim 1, wherein the first tube (11) comprises a guidewire lumen (12).

7. The deployment system (10) according to claim 1, wherein it further comprises:
    a shaft (32) disposed about and concentrically aligned with the first tube (11), wherein the shaft (32) is non-slidably positioned between the sheath (15) and the first tube (11), and is capable of engaging with the distal end (22) of the prosthesis (20).

8. The deployment system (10) according to claim 1, wherein it further comprises a tubular knurled rod (36) disposed about and concentrically aligned with a proximal portion of the sheath (15).

9. The deployment system (10) according to claim 8, wherein the tubular knurled rod (36) comprises at least one fixation element (37, 38), permitting releasable attachment of the tubular rod (36) with an abutment element (30).

10. The deployment system (10) according to claim 1, further comprising a cardiac valve prosthesis (20).

* * * * *